United States Patent [19]

Nguyen et al.

[11] Patent Number: 5,781,230
[45] Date of Patent: Jul. 14, 1998

[54] METHOD AND APPARATUS FOR ILLUMINATING TRANSLUCENT AND SEMI-TRANSPARENT MATERIAL

[75] Inventors: Hung Ngoc Nguyen, Bensalem, Pa.; Ralph A. Treder, Ewing, N.J.

[73] Assignee: Lucent Technologies, Inc., Murray Hill, N.J.

[21] Appl. No.: 790,481

[22] Filed: Jan. 29, 1997

Related U.S. Application Data

[63] Continuation of Ser. No. 358,482, Dec. 19, 1994, abandoned.

[51] Int. Cl.$^6$ .................................................. H04N 7/18
[52] U.S. Cl. ..................... 348/128; 348/127; 348/129; 348/88; 348/89
[58] Field of Search .......................... 348/128, 129, 348/127, 131, 88, 89

[56] References Cited

U.S. PATENT DOCUMENTS

| | | | |
|---|---|---|---|
| 4,688,939 | 8/1987 | Ray | 356/237 |
| 5,016,099 | 5/1991 | Bongardt et al. | 348/127 |
| 5,058,178 | 10/1991 | Ray | 382/8 |
| 5,166,753 | 11/1992 | Tokura | 348/128 |
| 5,208,645 | 5/1993 | Inoue et al. | 356/73.1 |
| 5,268,735 | 12/1993 | Hayashi | 348/128 |
| 5,305,710 | 4/1994 | Bashkansky et al. | 128/665 |
| 5,367,174 | 11/1994 | Bazile et al. | 356/237 |
| 5,432,461 | 7/1995 | Henley | 348/129 |
| 5,440,385 | 8/1995 | Fein et al. | 356/240 |
| 5,539,514 | 7/1996 | Shishido et al. | 356/237 |

Primary Examiner—Tommy P. Chin
Assistant Examiner—Anand Rao

[57] ABSTRACT

A machine vision system and method of enhancing the imaging of an article which is comprised of optically translucent or semi-transparent material. Generally, the system includes a vision processor, a video camera, a computer, and an illuminator. The illuminator directs light, in a three dimensional space, at a surface of the material other than a surface to be imaged. The light which enters the translucent material is scattered isotropically within the material and emerges from the surface to be imaged, in effect illuminating the material. The illumination enhances contrast, that can be typically achieved with conventional lighting, between the material and its background or adjoining components permitting the machine vision system to clearly image and detect features of the article.

15 Claims, 4 Drawing Sheets

METHOD AND APPARATUS FOR ILLUMINATING TRANSLUCENT AND SEMI-TRANSPARENT MATERIAL

This is a Continuation of application Ser. No. 08/358,482 filed Dec. 19, 1994, now abandoned.

BACKGROUND OF THE INVENTION

1. Field of the Invention

The present invention relates to machine vision systems. More particularly, the present invention relates to a machine vision system and method for illuminating the optically translucent and semi-transparent material of an article to be imaged.

2. Related Art

Machine vision is generally the automatic acquisition and analysis of images to obtain data for interpreting a scene or controlling an activity. Machine vision systems are extensively utilized in the manufacturing environment since such systems provide cost-effective means for performing assembly, automated inspection, gauging, recognition, and process control. The employment of machine vision has facilitated significant improvements in both product quality and manufacturing cost. These improvements are attributable, in part, to the elimination of human factors that affect reliability, such as fatigue, boredom, and inconsistency of judgment.

For instance, in the optics and microelectronics industries, machine vision systems are used in conjunction with robotics to observe and coordinate the assembly of optic or electronic components. Often these components or sub-assemblies are quite compact and require alignment tolerances that routinely range from several mils to a micron. Correspondingly, it is critical that these machine vision systems are capable of detecting the precise location of component features, such as the electrical contacts of an integrated circuit which are to be soldered to a printed circuit board or the respective edges of two sub-assemblies to be aligned.

Typically these components are composed of materials that range any where on the optical continuum from opaque (a medium which does not permit the passage of ordinary light or permit objects to be seen through it) to highly transparent materials (a medium which permits both the passage of ordinary light and objects to be seen distinctly through it). While opaque components can be rather easily imaged, highly transparent components can be exceedingly difficult to image. Between these two extremes, however, are translucent or semi-transparent materials. Translucent or semi-transparent media permit the passage of ordinary light but do not permit objects to be seen distinctly through the material. Translucent material can be either monocrystalline in structure (e.g., sapphire crystal) or polycrystalline (e.g., aluminum oxide, yttrium aluminum garnet, zirconium oxide, or zirconium silicate).

Presently, the machine vision system detection of translucent component features has been difficult because of a lack of contrast. That is, to accurately image any component feature, the degree of contrast between the feature with its background is an important factor. Contrast can be controlled, in part, by arranging the machine vision system's lighting and cameras in such a manner to distinguish each component feature from its background. While such techniques are effective with purely opaque components, they are generally not adequate with components of translucent material.

Accordingly, two conventional approaches have been employed to handle translucent material in the machine vision environment. The first entails altering the imaged surface of the translucent component with a coating or stain to render it a special color. The particular stain/color typically is chosen to enhance the contrast of the translucent component with its background and those components it adjoins, thus permitting the translucent component to be seen more distinctly by the conventional machine vision system. For example, to achieve the desired contrast between a translucent component and the components it adjoins, the translucent component can be coated with a stain that absorbs those wavelengths which are normally reflected efficiently by the adjoining components and reflect light at substantially different wavelengths. When necessary, further contrast enhancements are achieved with the use of a band-pass filter on the imaging camera. Such a filter, in effect, sensitizes the camera to only the light reflected off the coated surfaces of the translucent component by attenuating the intensity of those light wavelengths reflected from the adjoining components.

A second approach is to add dopants to the translucent material itself. When appropriately illuminated the material becomes fluorescent, distinguishing the material from its surroundings.

These conventional approaches, however, have several drawbacks. The coating, staining, and doping entail further processing, thereby increasing the cost associated with each component. Furthermore, the translucent material is typically selected for its particular inherent characteristics. For example, it may be that the translucent quality itself is a product requirement, thus any alteration simply cannot be tolerated. Similarly, in many instances, the translucent material is selected for its thermal conductive and electrical insulating properties which are likely to be significantly altered with the interjection of dopants.

In addition, use of a band-pass camera filter not only adds cost to the machine vision system, but also furthers its complexity. In practice, each machine vision system is typically used either for several different products or different stages of a product's assembly. It is only desirable to use such filters in those instances when translucent components are involved because the filters generally degrade the imaging performance of the system. Accordingly, mechanical means (rotary discs, plungers, and similar actuators) and sensors are required to physically position the filter in/out of the field of view of the camera.

SUMMARY OF THE INVENTION

The invention is a machine vision system and method for enhancing the imaging of an article which is comprised of optically translucent or semi-transparent material. The machine vision system, according to the preferred embodiment, includes a vision processor, video cameras, a computer, a robotics controller, a robotics arm, and an illuminator.

To facilitate enhanced imaging of translucent material, the material is optically irradiated to improve the contrast between it and its background or adjoining components. The illuminator, by directing a light ray on any surface of the translucent material, other than the imaged surface, causes light to enter the material and be scattered isotropically within the material. The light rays emerging from the translucent material's surface, when captured and imaged by the vision system, cause the bare material to be uniquely distinguishable from background materials or opaque features on the material's surface. Thus, the invention provides a low cost means of achieving enhanced imaging capabilities of translucent materials without physically altering the surfaces or properties of the material.

The foregoing, and other features and advantages of the invention will be apparent from the following, more particular description of the preferred embodiments of the invention, as illustrated in the accompanying drawings.

DETAILED DESCRIPTION OF THE PREFERRED EMBODIMENTS

The preferred embodiments of the invention are discussed in detail below. While specific model numbers and/or configurations are discussed, it should be understood that this is done for illustration purposes only. A person skilled in the relevant art will recognize that other components and configurations may be used without departing from the spirit and scope of the invention.

The preferred embodiments of the invention are now described with reference to the figures where like reference numbers indicate like elements. Also in the figures, the left most digit of each reference number corresponds to the figure in which the reference number is first used.

To illustrate the various features and aspects of the invention, the first preferred embodiment entails the relevant aspects of the AT&T Autobonder System. This system involves, in part, the use of a machine vision system to assemble optical repeater 100 used in underwater cable applications. As will be discussed with reference to FIG. 3, one of the components of optical repeater 100 has translucent properties.

Other machine vision embodiments of the invention include, for example, the assembly of flat panel displays, which typically involves the aligning and bonding of translucent and semi-transparent components or the assembly and inspection of microelectronic circuits. The invention, however, is not limited to machine vision embodiments. For example, the invention can be practiced with various manual or semi-automated processes which entail inspection or assembly of translucent material.

Optical repeater 100 includes primarily two components, an optical repeater sub-assembly 102 and a laser chip 104. In practice, the assembly of optical repeater 100 requires that laser chip 104 be precisely positioned, within a several micron tolerance, on sub-assembly 102 to ensure that an output, a laser beam (not shown), is properly positioned to avoid solder wetting of critical surfaces during solder reflow, and yet ensure adequate bonding surface overlap for heat sinking (dissipation).

Figure 2:
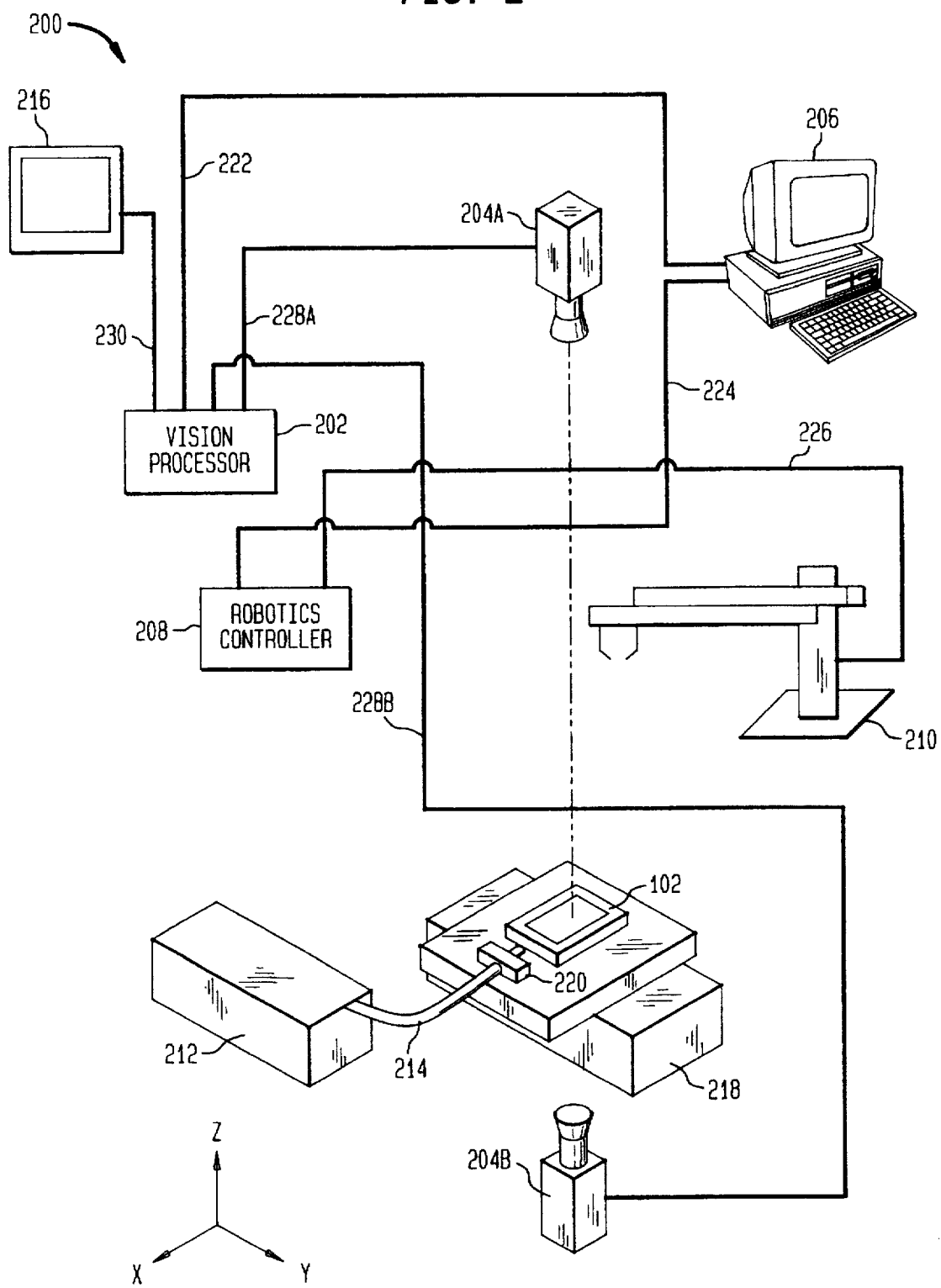
FIG. 2 is a high level block diagram illustrating a machine vision system 200, according to the present invention.

FIG. 2 illustrates a high level block diagram of a machine vision system 200, according to the present invention, used to assemble and inspect articles, such as optical repeater 100. The main components of machine vision system 200 include a vision processor 202, video cameras 204A and 204B (collectively 204), a computer 206, a robotics controller 208, a robotics arm 210, and an illuminator 212. A granite block 218 is used to support optical repeater sub-assembly 102 and to dampen vibrations.

Components for assembly (e.g., sub-assembly 102 and laser chip 104) are brought to machine vision system 200 by automatic feeders (not shown). Through image data received from cameras 204 and processed by vision processor 202, computer 206 coordinates the assembly via robotics controller 208 and robotics arm 210.

In practice, machine vision system 200 is generally autonomously controlled by computer 206. Computer 206 is a general purpose computer, such as a NCR 3333 from NCR Corporation, 1700 S. Patterson Boulevard, Dayton, Ohio 45479-0001. Control is facilitated by the communication of command sequences and data over two RS-232 links, 222 and 224, to vision processor 202 and robotics controller 208, respectively.

In this embodiment, each camera 204 is preferably a model TM-7 from Pulnix America, Inc., 1330 Orleans Drive, Sunnyvale, Calif. 94089-1135. However, any charge coupled or charge injected device can be used with the invention.

Vision processor 202 establishes the precise location of components and component features for assembly or inspection by processing the image data it receives from a output of each camera 204. The video output of each camera 204 is coupled to vision processor 202 by video links 228A and 228B (collectively 228). Vision processor 202, is preferably a Cognex 3400 from Cognex Corporation, 15 Crawford Street, Needham, Mass. 02194. A video monitor 216, is also coupled to vision processor 202 by a video link 230 to allow a technician to observe the field of view of cameras 204.

The movement and placement of components such as sub-assembly 102, to/from granite block 218 is facilitated by robotics arm 210. In this embodiment, robotics controller 208 is an Anorad 5000, from Anorad Corporation, 110 Oser Avenue, Hauppauge, N.Y. 11788-3871.

Generally, vision system 200 can be used with various lighting sources. For example, top-down lighting and/or bottom-up lighting can be used (i.e., lighting from above and below sub-assembly 102 along the Z-axis). Top-down lighting is generally advantageous for component location and inspection. Bottom-up lighting, is well suited for highlighting the detailed features of the components or their relative positions during assembly. Although not shown in FIG. 2, vision system 200 utilizes both top-down and bottom-up lighting in conjunction with down-looking camera 204A and up-looking camera 204B, respectively.

Illumination of sub-assembly 102, itself, is provided by illuminator 212. As will be discussed in detail with reference to FIGS. 3–5, a goose necked fiber bundle 214 directs a substantially white light ray 310 onto sub-assembly 102. Alternatively, however, the invention can be practiced with a monochromatic light source. Illuminator 212 is preferably a Fiberoptics FO-150 from Fiberoptics Technology, Inc., 1 Fiber Road, Pomfret, Conn. 06258. Generally, the light ray 310 should be constrained to avoid stray light reaching cameras 204. In this embodiment, fiber bundle 214 is approximately ¼" in diameter, and light ray 310 is substantially cone shaped, with a half-angle of approximately 15°. A fiber bundle fixture 220 adjustably mounts the end of fiber bundle 214 to block 218 forming the desired positioning of light ray 310. Alternatively, a light fixture mounted on block 218 itself, instead of the combination of illuminator 212, fiber bundle 214, and bundle fixture 220 can be used without deviating from the spirit of the invention.

Figure 1:
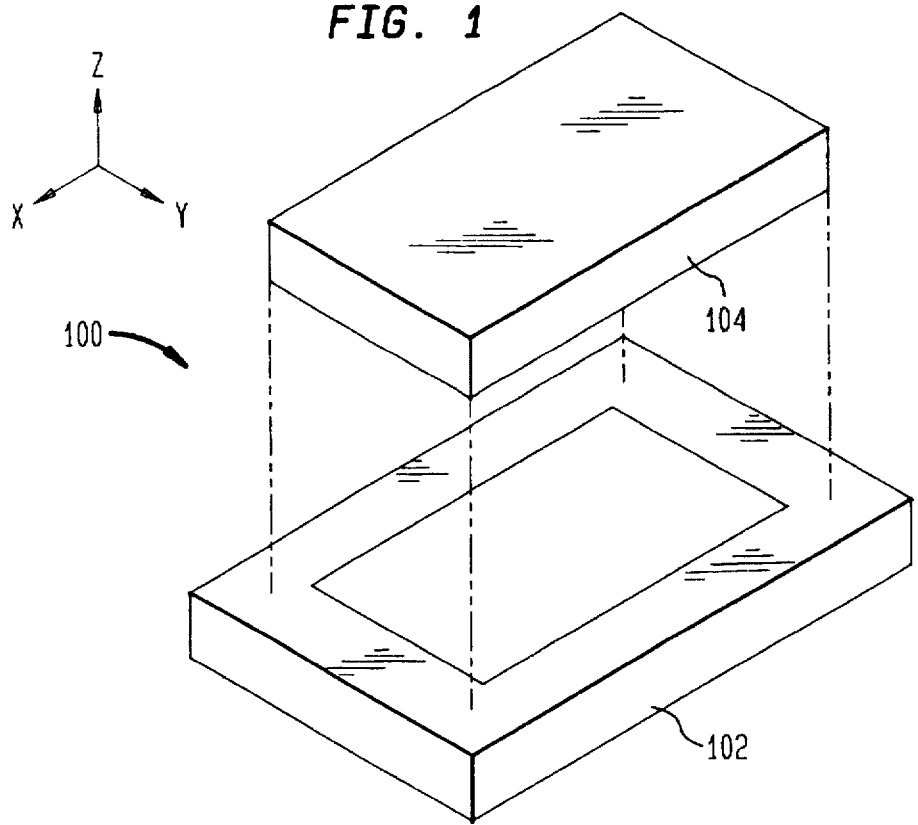
FIG. 1 is a perspective view of an optical repeater 100.
Figure 3:
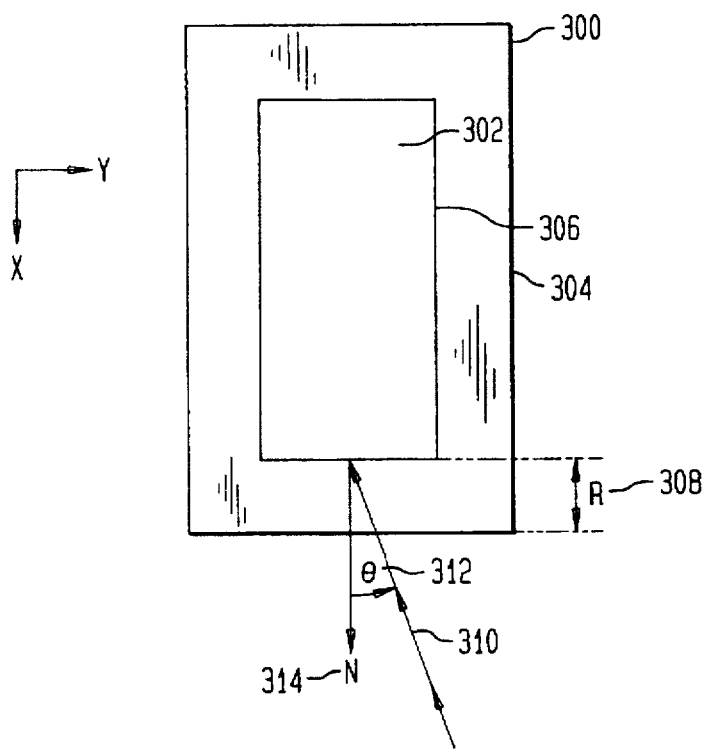
FIG. 3 is a top view of a substrate 300 exposed to a light ray 310 in the XY-plane.

FIG. 3 illustrates a top view of sub-assembly 102 on which laser chip 104 is aligned and placed during assembly. Sub-assembly 102 is generally comprised of at least two materials, a sintered beryllium oxide (BeO) substrate 300 and a patterned gold film/flashing 302. During assembly, laser chip 104 is positioned on top of gold film 302 with the edges of laser chip 104 nominally in line with edges 304 of substrate 300. Laser repeater 100 utilizes these two materials for their thermal and electrical properties. That is, the BeO material is used because it inherently has thermal conducting and electrical insulating properties particularly suited for laser components. As with laser components generally, laser chip 104 generates a considerable amount of heat which must be drawn away from it, by the BeO substrate 300, to a heat sink (not shown). This prevents heat build-up which may alter the characteristics of laser chip 104. Substrate 300 also provides the required electrical isolation between laser chip 104 and the other components of optical repeater 100 (not shown). On the other hand, gold film 302 is used in sub-assembly 102 for its good electrical attributes as a bonding surface for laser chip 104.

While these materials were selected for the above discussed characteristics, they also have two additional attributes which are relevant to the present invention. Namely, substrate 300 is optically translucent and gold film 302 is opaque to visible and near visible light. It is these characteristics which impede conventional machine vision systems from properly aligning laser chip 104 with sub-assembly 102. In particular, with reference to FIG. 3, a region 308 between each outer edge 304 of substrate 300 and its corresponding parallel edge 306 of gold film 302 is of interest. Conventional machine vision systems, particularly those with top-down lighting schemes, are generally inadequate because of their inability to locate outer edges 304 of substrate 300. That is, since gold film 302 is opaque, substantially smooth, and highly reflective it is easily imaged by a conventional vision system with camera viewing along the Z-axis. The exposed portion of substrate 300 or region 308, however, is translucent and substantially absorbs the top-down lighting. As a result edges 304 are barely detectable. Moreover, if region 308 is particularly narrow (e.g., less than 1 mil) a "blooming" effect occurs whereby the light reflecting from gold film 302 blinds cameras 204 to both edges 304 and 306. While high speed shutters might be expediently employed to reduce the light intensity from gold film 302 and improve detection of edges 306, such a technique may only serve to reduce the total light received from all features in the field of view, including substrate 300 and edges 304. In particular, this type of technique can prove to be unsatisfactory since the contrast between gold film 302 and substrate 300 can be practically as high as the contrast between gold film 302 and empty space (where there are no light reflections).

Figure 4:
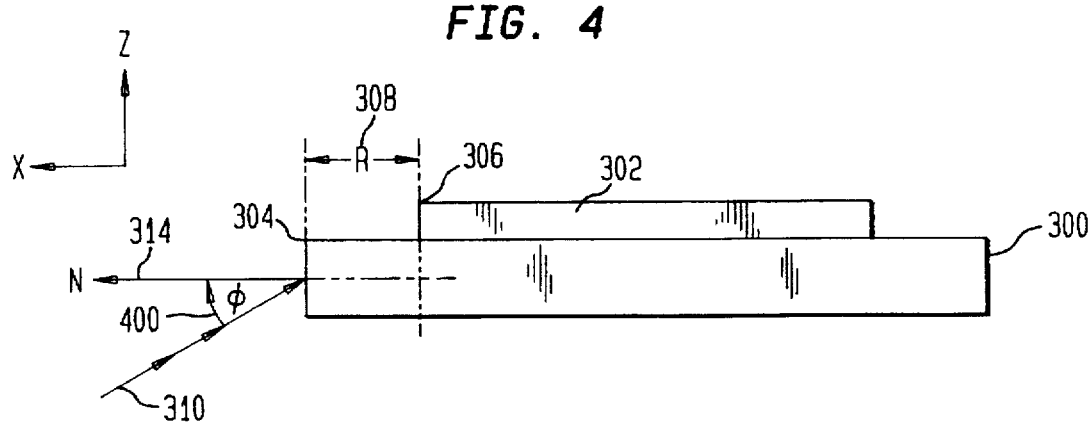
FIG. 4 is a side view of a substrate 300 exposed to a light ray 310 in the XZ-plane.

As illustrated in FIGS. 3–5, the present invention enhances the detection of the attributes (in this embodiment the edges 304 and 306) of sub-assembly 102 by directing light ray 310 at a side wall 500 of substrate 300. In this manner, substrate 300 is caused to self-illuminate or "glow", providing an easily detected signature of its spatial extent for capture by cameras 204. The enhanced detectability, in turn, permits vision system 200 to distinctly detect edges 304 and 306 and thus precisely align laser chip 104 with sub-assembly 102.

In this embodiment, light ray 310 impinges side wall 500 in a three dimensional XYZ-space. Specifically, with reference to the XY-plane of FIGS. 3 and 5(a)–(b), illuminator 212, via fiber bundle 214, introduces light ray 310 to side wall 500 at an angle Θ 312 from a normal vector (N) 314. Similarly, with reference to FIGS. 4 and 5(a)–(b), angle Θ 400 represents the introduction of light ray 310, in the XZ-plane. Angles Θ 312 and Ø 400 are approximately 60° and 20°, respectively. The values of these angles were selected empirically to achieve the desired contrast to image edges 304 and 306 in the AT&T Autobonder System. The setting of angle Ø 400 tends to be more critical than that of angle Θ 312. Generally, angle Ø 400 ensures that an adequate portion of light ray 310 is directed upwardly (along the Z-axis) toward the imaged surface 504 through the bulk of substrate 300. As angle Ø 400 approaches 90° in the XZ-plane, however, excess light can radiate from substrate 300 and blind cameras 204.

Figure 5A:
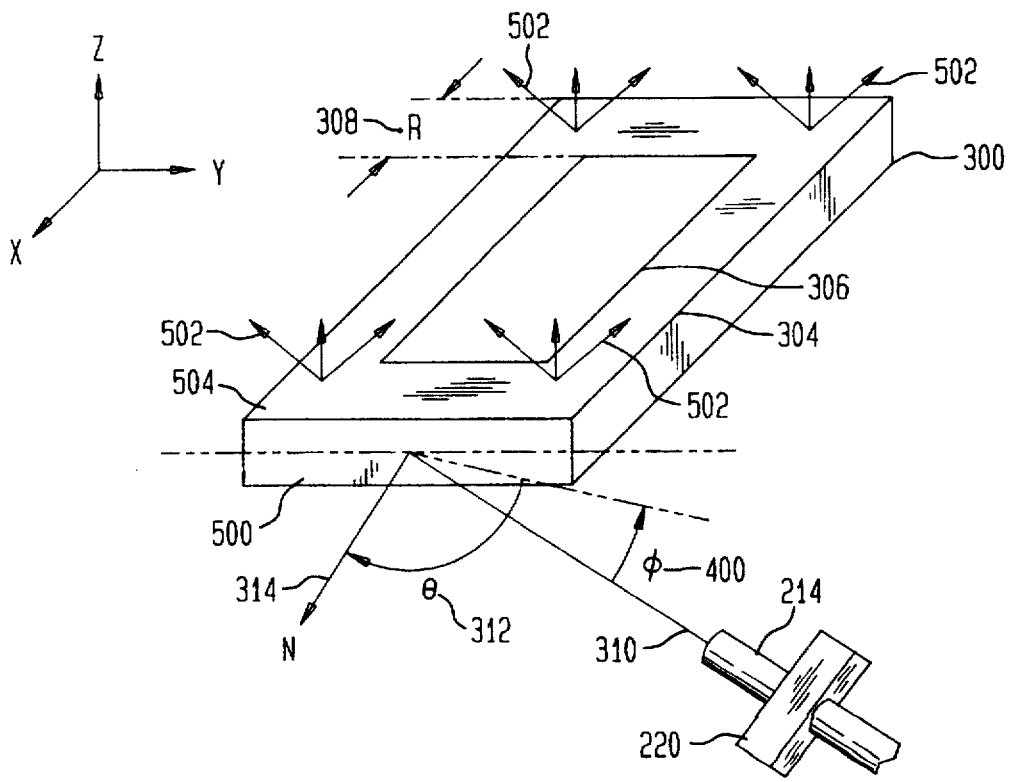
FIGS. 5(a)–(b) are perspective views of a substrate 300 exposed to a light ray 310 in the XYZ-space.
Figure 5B:
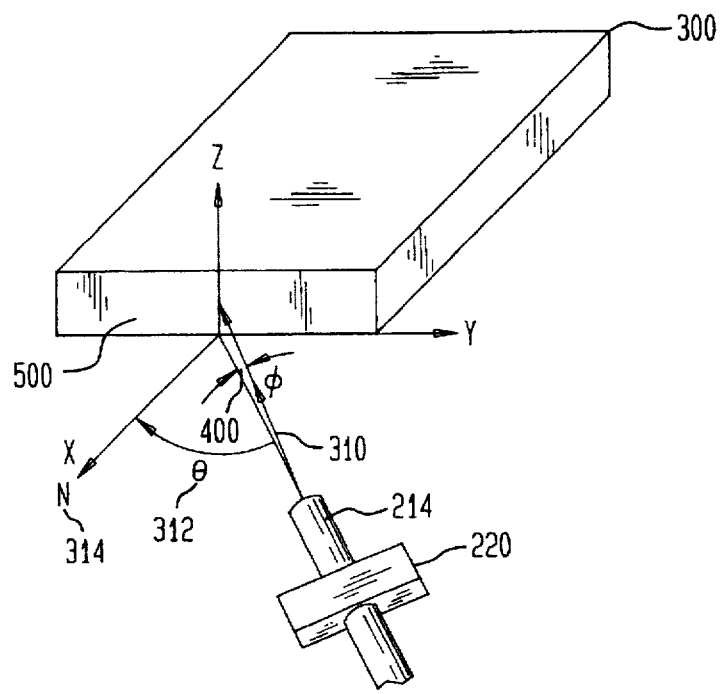

FIGS. 5(a)–(b) illustrate the resulting "glowing" effect which clearly delineates region 308 and edges 304 and 306 for imaging. The effect is caused, in part, by the inherent polycrystalline structure of the substrate 300 BeO material. That is, adjacent crystals in the BeO have different, largely random crystallographic orientations. Correspondingly, there are variations in the index of refraction along any straight-line path (e.g., in the XY-plane) through the bulk of substrate 300. Thus, light ray 310 is scattered within substrate 300 in a multiplicity of directions causing a "glowing" effect from surface light rays 502 which radiate from the bulk of substrate 300 (in particular, imaged surface 504 or the surface normal to the Z-axis).

Moreover, edges 304 are now definitely detectable by the virtual absence of light beyond these edges. Cameras 204, particularly top-down camera 204A, can now detect the location of each edge 304 by the enhanced contrast between region 308 and the background of substrate 300 or the area beyond each edge 304.

While this embodiment illustrates the introduction of light ray 310 at angles Θ 312 and Ø 400, it would be obvious to one skilled in the art that the values of these angles are design parameters and may vary with application to achieve the desired effect. Additionally, the present invention could be practiced with light rays introduced at multiple surfaces of the translucent material.

Figure 6:
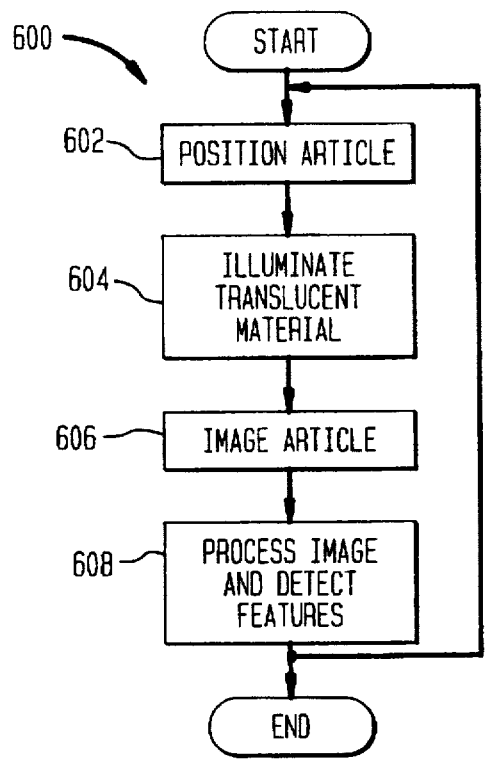
FIG. 6 is a flow diagram 600 illustrating a method of illuminating the optically translucent or semi-transparent material of an article to be imaged.

FIG. 6 is a flow diagram 600 illustrating a method of illuminating the optically translucent or semi-transparent material of an article to be imaged. In step 602, the article is positioned with the surface to be imaged (the first surface) in the Z-axis. In step 604, the translucent material is illuminated by directing a light source at another surface of the material (second surface) at a first angle from a normal in the XY-plane and a second angle from the normal in the XZ-plane. In step 606, an image of the first surface is captured. In step 608, the image is processed to locate the features of the first surface. Although steps 606–608 are generally applicable for use with machine vision systems, the present invention is not limited only to such embodiments. For example, the invention can be practiced by a technician to manually assemble or inspect an article by performing only steps 602–604.

While the invention has been particularly shown and described with reference to several preferred embodiments thereof, it will be understood by those skilled in the art that various changes in form and details may be made therein without departing from the spirit and scope of the invention as defined in the appended claims.

What is claimed is:

1. An apparatus for imaging a translucent article comprising a translucent metal oxide substrate and an opaque metallic film on an imaged surface of the substrate, the apparatus comprising:
    image capturing means trained on said imaged surface of the translucent article for capturing all image thereof; and
    illuminating means for directing a light ray at a first sidewall of the translucent article, said illuminating means being below a plane of the imaged surface,
    wherein said light ray enters the translucent article and illuminates said imaged surface, thus making said imaged surface capable of being distinctly imaged by said image capturing means, and
    wherein no light ray is directed at the imaged surface or a surface directly opposite said imaged surface.

2. The apparatus according to claim 1, further comprising a second illuminating means for directing a second light ray at a second sidewall of the translucent article.

3. The apparatus according to claim 1, wherein said light ray is directed to enter the translucent article at an angle having a first angular component with respect to a first normal of said imaged surface and a second normal of said first sidewall and a second angular component with respect to said second normal.

4. The apparatus according to claim 3, wherein:
    said first angular component is about 20 degrees from said second normal in a first plane formed by said first and second normal; and
    said second angular component is about 60 degrees from said second normal in a second plane substantially parallel to said imaged surface.

5. The apparatus according to claim 1, wherein said light ray is substantially white light.

6. A machine vision system for imaging a translucent article comprising a translucent metal oxide substrate and an opaque metallic film on an imaged surface of the substrate, the system comprising:
    means for supporting the translucent article;
    camera substantially trained on said imaged surface of the translucent article for capturing an image of said imaged surface;
    a vision processor operably coupled to said camera for processing image information; and
    illumination means for directing a light ray at a first sidewall of the translucent article, said illuminating means being below a plane of said imaged surface and said light ray entering said first sidewall with a first angular component in a first plane formed by a first normal of said imaged surface and a second normal of said first sidewall and a second angular component in a second plane substantially parallel to said imaged surface,
    wherein said light ray illuminates the translucent article and enhances said imaged surface for imaging by said camera and said vision processor, and
    wherein no light ray is directed at the imaged surface or a surface directly opposite said imaged surface.

7. The machine vision system according to claim 6, wherein:
    said first angular component is about 20 degrees from said second normal in said first plane; and
    said second angular component is about 60 degrees from said second normal in said second plane.

8. The machine vision system according to claim 6, wherein said illumination means is a monochromatic light source.

9. A method of illuminating an imaged surface of an optically translucent article for imaging comprising a translucent metal oxide substrate and an opaque metallic film at said imaged surface, the method comprising the steps of:
    directing a visible light ray from a source below a plane of said imaged surface at a first sidewall of the translucent article such that said light ray enters the translucent article and illuminates the imaged surface that is to be imaged; and
    capturing an image of the imaged surface,
    wherein no light ray is directed at the imaged surface or a surface directly opposite said imaged surface.

10. The method according to claim 9, wherein said light ray is directed to enter the translucent article at an angle having a first angular component with respect to a first normal of the imaged and a second normal of said first sidewall and a second angular component with respect to said second normal.

11. The method according to claim 10, wherein:
    said first angular component is about 20 degrees from said second normal in a first plane formed by said first and second normal; and
    said second angular component is about 60 degrees from said second normal in a second plane substantially parallel to said first sidewall.

12. The apparatus according to claim 1, wherein the opaque metallic film comprises gold.

13. The apparatus according to claim 12, wherein the translucent metal oxide substrate comprises beryllium oxide.

14. The machine vision system according to claim 6, wherein the opaque metallic film comprises gold.

15. The machine vision system according to claim 14, wherein the translucent metal oxide substrate comprises beryllium oxide.

* * * * *